United States Patent [19]

Schaarschmidt et al.

[11] Patent Number: 4,991,450
[45] Date of Patent: Feb. 12, 1991

[54] FILLING ARRANGEMENT FOR TAKING A SAMPLE OF A RADIOACTIVE PROCESS SOLUTION

[75] Inventors: Ulrich Schaarschmidt, Stutensee; Wolfgang Haut, Waghausel, both of Fed. Rep. of Germany

[73] Assignee: Deutsche Gesellschaft für Wiederaufarbeitung von Kernbrennstoffen mbH, Hanover, Fed. Rep. of Germany

[21] Appl. No.: 369,136

[22] Filed: Jun. 21, 1989

[30] Foreign Application Priority Data

Jun. 28, 1988 [DE] Fed. Rep. of Germany ....... 3821706

[51] Int. Cl.$^5$ .............................................. G01N 1/00
[52] U.S. Cl. .................................................. 73/863.61
[58] Field of Search ........... 73/863.41, 863.61, 863.71, 73/863.81, 863.83, 863.85, 863.86, 864.33, 864.34, 864.73

[56] References Cited

U.S. PATENT DOCUMENTS

| 3,597,978 | 8/1971 | Siclari et al. | 73/863.86 |
| 3,813,223 | 5/1974 | Elmer | 422/102 |
| 4,118,987 | 10/1978 | Zeh | 73/863.61 |
| 4,638,675 | 1/1987 | Sperinck et al. | 73/864.73 |
| 4,651,574 | 3/1987 | Spencer | 73/863.86 |
| 4,674,343 | 6/1987 | Larson | 73/863.86 |
| 4,800,761 | 1/1979 | Spencer | 73/863.71 |

FOREIGN PATENT DOCUMENTS 7606823 9/1976 Fed. Rep. of Germany .

OTHER PUBLICATIONS

"Chemische Laboratoriumsgeräte" by Dr.-Ing. Wolfgang Telle, 2., verbesserte Auflage, VEB Deutscher Verlag für Grundstoffindustrie, Leipzig 1969, p. 132.

Primary Examiner—Robert Raevis
Attorney, Agent, or Firm—Walter Ottesen

[57] ABSTRACT

The invention is directed to a filling arrangement for taking samples of radioactive process solutions from a liquid flow. The filling arrangement includes a filling head having a through-flow bore. The bore has a constriction in its cross section with first and second passages branching off from the through-flow bore forward of and rearward of the constriction, respectively. To reduce the risk of obstruction when samples of radioactive liquids containing solids are taken, the filling passages are formed so as to be mutually adjacent. The passages are open at the end remote from the through-flow bore and terminate in a conically tapered extension formed on the filling head. The open sample vessel is pushed over the conically tapered extension when taking a sample.

2 Claims, 1 Drawing Sheet

FILLING ARRANGEMENT FOR TAKING A SAMPLE OF A RADIOACTIVE PROCESS SOLUTION

FIELD OF THE INVENTION

The invention relates to a filling arrangement for taking a sample of a radioactive process out of liquid flow. The sample is taken in a sample vessel with a filling head having a through-flow bore with a constriction. Filling openings are provided forward and rearward of the constriction.

BACKGROUND OF THE INVENTION

When nuclear fuels are reprocessed, fuel solutions are formed during dissolution which can contain undissolved solids having a grain size in the range of $10^{-4}$ mm to 5 mm. It is essential to be able to obtain samples that are representative of these suspensions.

Known sampling devices in reprocessing facilities use a combination of a sealed sample vessel and a hollow needle filling means to transfer the sample of the solution into sample vessels. The filling port of the vessel is sealed by a rubber septum through which one or two hollow needles are inserted; these needles are ground to an acute angle. The vessel is filled through the inserted needles.

When the filled vessel has been pulled off the hollow needle or needles, the resilient rubber septum closes the place of incision. The material is only incised rather than being punched out because of the special grind of the needles and because of the needle diameter of up to about 2.5 mm. Larger needle diameters cannot be used, as they would punch material out of the septum, and the openings formed thereby could not reclose when the needles are withdrawn. Accordingly, suspensions having a maximum particle size of about 2 mm can be filled into vessels as representative samples with the rubber-septum/hollow-needle combination. If there are larger solid particles in the suspension, obstructions will develop or non-representative samples will be obtained.

German published patent application DE-AS 2,614,787 discloses an apparatus for taking radioactive liquid samples and with which a sample can be taken from a radioactive liquid circuit. In this apparatus, the problem of a blockage in the hollow needles by the solid particles of the liquid is said to be solved in that the hollow needles subjected to blockage are arranged and configured so that they can be exchanged far more easily.

SUMMARY OF THE INVENTION

It is an object of the invention to reduce the danger of blockage in the sampling of radioactive liquids containing solids thereby minimizing the frequency of maintenance.

In the filling arrangement according to the invention, filling passages of larger cross section are used instead of hollow needles. These passages are formed in the filling head which has a conically tapered extension formed at the bottom thereof. An open sample vessel to be filled is pressed without a membrane against the lower extension of the filling head in a seal-tight manner. The vessel is filled with the suspension through one of the filling passages which functions as a feed passage; whereas, the other passage functions as a return passage through which the surplus suspension is passed back into the main flow discharged from the filling head through an outlet port.

The suspension containing solids can flow through the two mutually adjacent passages without the problem of a blockage occurring; these two passages are perpendicular to the through-flow bore. The external conically tapered extension acts as a filling cone. The area of the opening of the sample vessel is always slightly larger than the cross-sectional area available in the filling cone.

The filling passages within the filling head can be configured to have various shapes and cross sections. The through-flow volume can be affected by varying the configuration of the cross sections.

Samples can be taken from different media with the filling head according to the invention which contains the feed and return passages. Almost any solid-liquid mix phases may be filled into vessels from a pipe line. The filling arrangement according to the invention may also be used advantageously in taking samples of liquid media containing liquid components having a high viscosity.

BRIEF DESCRIPTION OF THE DRAWINGS

The invention will now be explained with reference to the accompanying drawings wherein.

DESCRIPTION OF THE PREFERRED EMBODIMENTS OF THE INVENTION

Figures 1, 2:
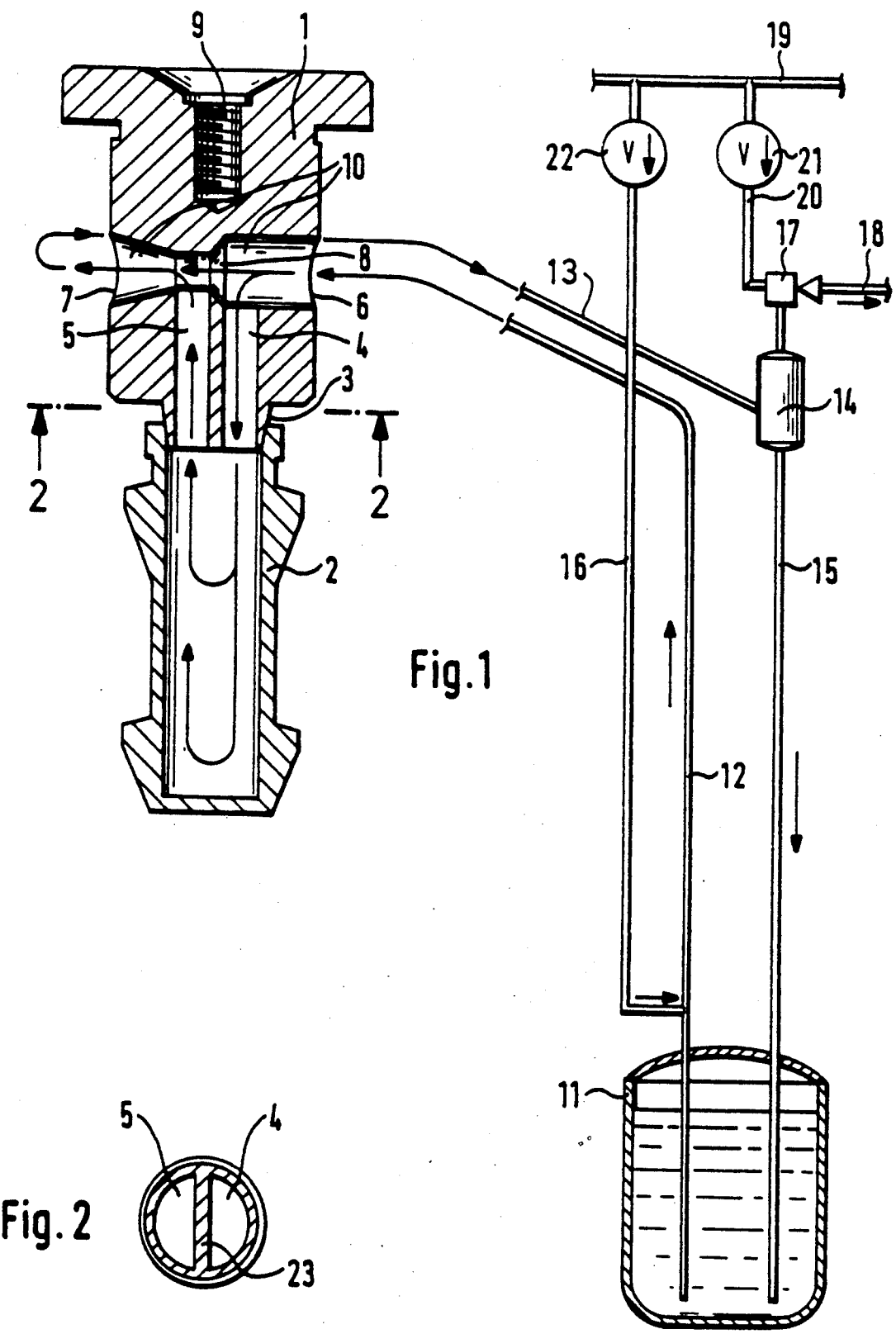
FIG. 1 is a section view taken through a filling head with a sample vessel seated thereon and with the feed system to the head shown, schematically; and, FIG. 2 is a section view through the filling and docking cone taken along the line 2—2 in FIG. 1.

A docking cone 3 is formed at the bottom of the filling head 1 for filling the sample vessel 2. Open vessel 2 is pushed over the docking cone 3 with a seal-tight fit. The filling head 1 contains a feed passage 4 which extends along its longitudinal axis and acts as an inlet. A passage 5 adjacent the passage 4 is also open at the bottom and is a return passage. A main suspension flow is passed into the filling head 1 through an inlet port 6 and exits from the head 1 through an outlet port 7. The inlet and outlet ports (6, 7) are interconnected by a constriction 8 in the head 1.

The filling head 1 is held in a seat (not shown) which also contains the feed lines for the medium. A threaded bore 9 acts as a holder for inserting the head in its seat or removing it therefrom.

A through-flow bore 10 extending transversely to the longitudinal axis of the head 1 comprises the inlet port 6, the constriction 8 and the outlet port 7. The feed passage 4 is connected to the bore 10 forward of the constriction 8, and the return passage 5 rearward thereof.

The main flow is moved out of a process vessel 11 to the filling head 1 by a circulating feed with an under-pressure-aided airlift pumping system or with pumps. For this purpose, the process vessel 11 is provided with a pipe line 12 leading to the head 1 and connected to the inlet port 6. The outlet port 7 is connected to a pipe line 13 leading to a venting container 14 from which a return pipe 15 leads to the process vessel 11. An airlift device 16 which injects slugs of compressed air into the pipe 12 is provided to pump the process flow. The venting container 14 is connected to an ejector 17 fitted with a venting pipe 18 to generate an underpressure. The ejector 17 is supplied with compressed air from a compressed air pipe 19 through a pipe line 20 and a valve 21;

whereas, the airlift device 16 can also be connected to the compressed air pipe 19 by way of the valve 22.

A cross section through the docking cone 3 is shown in FIG. 2. The feed passage 4 and return passage 5 are separated from each other by a wall 23.

The apparatus described above operates in the manner explained below.

If no vessel 2 is docked on the filling head 1, the underpressure in the filling system collapses and the process liquid cannot be pumped.

In order to fill a sample vessel, the open vessel 2 is pushed over the docking cone 3 of the filling head 1 in a seal-tight manner. The ejector 17 becomes effective and generates an underpressure in the filling system which causes a column of liquid to form in the pipe line 12. The connection of the airlift 16 is made beneath the column of liquid. The feed of the medium to be sampled begins.

The suspension is filled into the vessel 2 through the pipe line 12, the inlet port 6 and the feed passage 4, since a component flow of the main flow of the suspension is diverted into the filling passages 4 and 5 by the constriction 8. The excess suspension is returned to the system through the outlet port 7 of the head.

When the vessel 2 has been filled, it is removed from the docking cone 3. The underpressure collapses and the circulating feed of the suspension stops abruptly. After the vessel 2 is removed, it is sealed either manually or by appropriate closure apparatus. The vessel 2 contains a sample which is representative of the liquid in the vessel 11.

It is understood that the foregoing description is that of the preferred embodiments of the invention and that various changes and modifications may be made thereto without departing from the spirit and scope of the invention as defined in the appended claim.

What is claimed is:

1. A filling arrangement for taking a sample of a radioactive process solution from a liquid flow, the filling arrangement comprising:

a sample vessel for receiving and holding the sample therein, said vessel having a connecting portion defining a filling opening through which the sample is passed into the interior of the vessel;

a filling head having a through-flow bore formed therein through which the liquid flow is passed when a sample is taken, said through-flow bore being configured so as to have a constricted segment;

first and second passages formed in said filling head so as to be mutually adjacent and having respective first ends opening into said through-flow bore forward of and rearward of said constricted segment, respectively;

said filling head having a docking extension formed thereon and said first and second passages being formed in said filling head so as to pass through said docking extension and having respective second ends formed and defining openings in said docking extension;

annular seat means formed on said docking extension;

said connecting portion of said vessel being configured so as to cause said filling opening to have a diameter to permit said connecting portion to be docked directly on said docking extension so as to be in direct contact engagement with said seat means; and, said connecting portion and said seat means being formed so as to conjointly define a seal-tight contact interface when said vessel is docked on said filling head for receiving the sample.

2. The filling arrangement of claim 1, said docking extension being a conically tapered docking extension and said annular seat means being formed on said conically tapered docking extension; and, said connecting portion of said sample vessel having a conically tapered surface formed thereon to define said opening and for contact engaging said seat means to define said seal-tight contact interface.

* * * * *